(12) United States Patent
Richard et al.

(10) Patent No.: US 9,427,380 B2
(45) Date of Patent: Aug. 30, 2016

(54) WEAR RESISTANT DENTAL COMPOSITION

(71) Applicant: SEPTODONT OU SEPTODONT SAS OU SPECIALITES SEPTODONT, Saint Maur des Fosses (FR)

(72) Inventors: Gilles Richard, Crosne (FR); Olivier Marie, Soisy sur Seine (FR); Laurianne Bafounguissa, Savigny-le-Temple (FR)

(73) Assignee: SEPTODONT OU SEPTODONT SAS OU SPECIALITES SEPTODONT, Saint Maur des Fosses (FR)

( * ) Notice: Subject to any disclaimer, the term of this patent is extended or adjusted under 35 U.S.C. 154(b) by 148 days.

(21) Appl. No.: 14/346,614

(22) PCT Filed: Sep. 21, 2012

(86) PCT No.: PCT/EP2012/068711
§ 371 (c)(1),
(2) Date: Mar. 21, 2014

(87) PCT Pub. No.: WO2013/041709
PCT Pub. Date: Mar. 28, 2013

(65) Prior Publication Data
US 2014/0224151 A1 Aug. 14, 2014

(30) Foreign Application Priority Data

Sep. 21, 2011 (EP) ..................... 11182238

(51) Int. Cl.
| A61K 6/00 | (2006.01) |
| A61K 6/06 | (2006.01) |
| A61C 19/00 | (2006.01) |
| C04B 14/30 | (2006.01) |
| C04B 14/38 | (2006.01) |
| C04B 14/26 | (2006.01) |
| C04B 22/06 | (2006.01) |
| C04B 7/345 | (2006.01) |
| C04B 16/08 | (2006.01) |
| C04B 16/06 | (2006.01) |
| C04B 16/00 | (2006.01) |

(52) U.S. Cl.
CPC ........... *A61K 6/0047* (2013.01); *A61C 19/005* (2013.01); *A61K 6/0073* (2013.01); *A61K 6/0091* (2013.01); *A61K 6/0612* (2013.01); *C04B 7/345* (2013.01); *C04B 14/26* (2013.01); *C04B 14/301* (2013.01); *C04B 14/38* (2013.01); *C04B 16/00* (2013.01); *C04B 16/06* (2013.01); *C04B 16/08* (2013.01); *C04B 22/064* (2013.01)

(58) Field of Classification Search
CPC .... A61K 6/0612; C04B 7/345; C04B 14/26; C04B 14/301; C04B 14/38; C04B 16/06; C04B 16/08; C04B 16/00; C04B 22/064
See application file for complete search history.

(56) References Cited

U.S. PATENT DOCUMENTS

| 2,122,011 A | 6/1938 | Czapp et al. ................ 106/6 |
| 2,901,377 A | 8/1959 | Hans Bode ................... 117/70 |
| 4,381,918 A | 5/1983 | Ehrnford et al. ............. 433/199 |
| 4,647,600 A | 3/1987 | Kawahara et al. ............. 433/28 |
| 5,415,547 A | 5/1995 | Torabinejad et al. ......... 433/228 |
| 5,584,926 A | 12/1996 | Borgholm et al. ........... 106/713 |
| 6,334,775 B2 | 1/2002 | Xu et al. ..................... 433/228 |
| 6,652,282 B2 | 11/2003 | Jensen et al. ................ 433/228 |
| 6,858,074 B2 | 2/2005 | Anderson et al. ............ 106/724 |
| 7,819,663 B2 | 10/2010 | Bergaya et al. .............. 433/226 |
| 7,942,961 B2 | 5/2011 | Asgary et al. ................. 106/35 |
| 8,974,586 B2 | 3/2015 | Richard et al. |
| 2002/0045678 A1 | 4/2002 | Lopez et al. ................. 523/115 |
| 2002/0198283 A1 | 12/2002 | Imai et al. ................... 523/116 |
| 2003/0121455 A1 | 7/2003 | Hermansson et al. ........ 106/692 |

(Continued)

FOREIGN PATENT DOCUMENTS

| CN | 1446530 | 10/2003 |
| DE | 19923956 | 11/2000 |

(Continued)

OTHER PUBLICATIONS

Kogan P. et al., "The effects of various additives on setting properties of MTA", Journal of Endodontics, vol. 32, N° 6, Jun. 2006, pp. 569-572.

(Continued)

*Primary Examiner* — Carol M Koslow
(74) *Attorney, Agent, or Firm* — Young & Thompson

(57) ABSTRACT

The present invention relates to a solid composition comprising: a calcium silicate powder, a set accelerator in the form of a powder, a reinforcing filler in a solid form, a radio-opacifying agent in a solid form, at least one complementary ingredient selected from solid fibers or solid porous fillers, optionally a water-reducing agent in a solid form, and optionally solid pigments. The present invention also relates to a kit of parts for the preparation of a composition suitable for use in dentistry comprising in a first container a solid phase including the solid composition according to the invention, and in a second container an aqueous phase. The present invention also relates to a kit of parts for the preparation of a composition suitable for use in dentistry comprising a container, said container comprising at least two cells, the first cell comprising a solid phase including the solid composition of the invention and the second cell comprising an aqueous phase. The present invention also relates to a method for preparing a dental cement, including mixing the solid composition of the invention with an aqueous phase and to resulting dental cement.

18 Claims, 1 Drawing Sheet

(56) References Cited

U.S. PATENT DOCUMENTS

| | | | |
|---|---|---|---|
| 2007/0009858 A1 | 1/2007 | Hatton et al. | 523/116 |
| 2007/0072957 A1 | 3/2007 | Noguchi et al. | 523/116 |
| 2008/0085948 A1 | 4/2008 | Primus et al. | 523/116 |
| 2008/0206716 A1* | 8/2008 | Asgary | A61K 6/0625 433/228.1 |
| 2008/0299093 A1* | 12/2008 | Yang | A61L 24/0015 424/93.7 |
| 2011/0281241 A1 | 11/2011 | Pandolfelli et al. | 106/35 |

FOREIGN PATENT DOCUMENTS

| | | |
|---|---|---|
| EP | 2555740 | 2/2013 |
| FR | 2603274 | 3/1998 |
| JP | 3165773 | 7/1991 |
| JP | 3183650 | 8/1991 |
| JP | 2003-286176 | 10/2003 |
| JP | 2004-051454 | 2/2004 |
| RU | 2197940 | 2/2003 |
| WO | 93/21122 | 10/1993 |
| WO | 01/76534 | 10/2001 |
| WO | 2005/087178 | 9/2005 |
| WO | 2007/047994 | 4/2007 |
| WO | 2008/000917 | 1/2008 |
| WO | 2008/100451 | 8/2008 |
| WO | 2008/102214 | 8/2008 |

OTHER PUBLICATIONS

Benz et al., "Effects of cement particle size distribution on performance properties of Portland cement based materials", Cement and Concrete Research, vol. 29, N° 10, Oct. 1999, pp. 1663-1671.

* cited by examiner

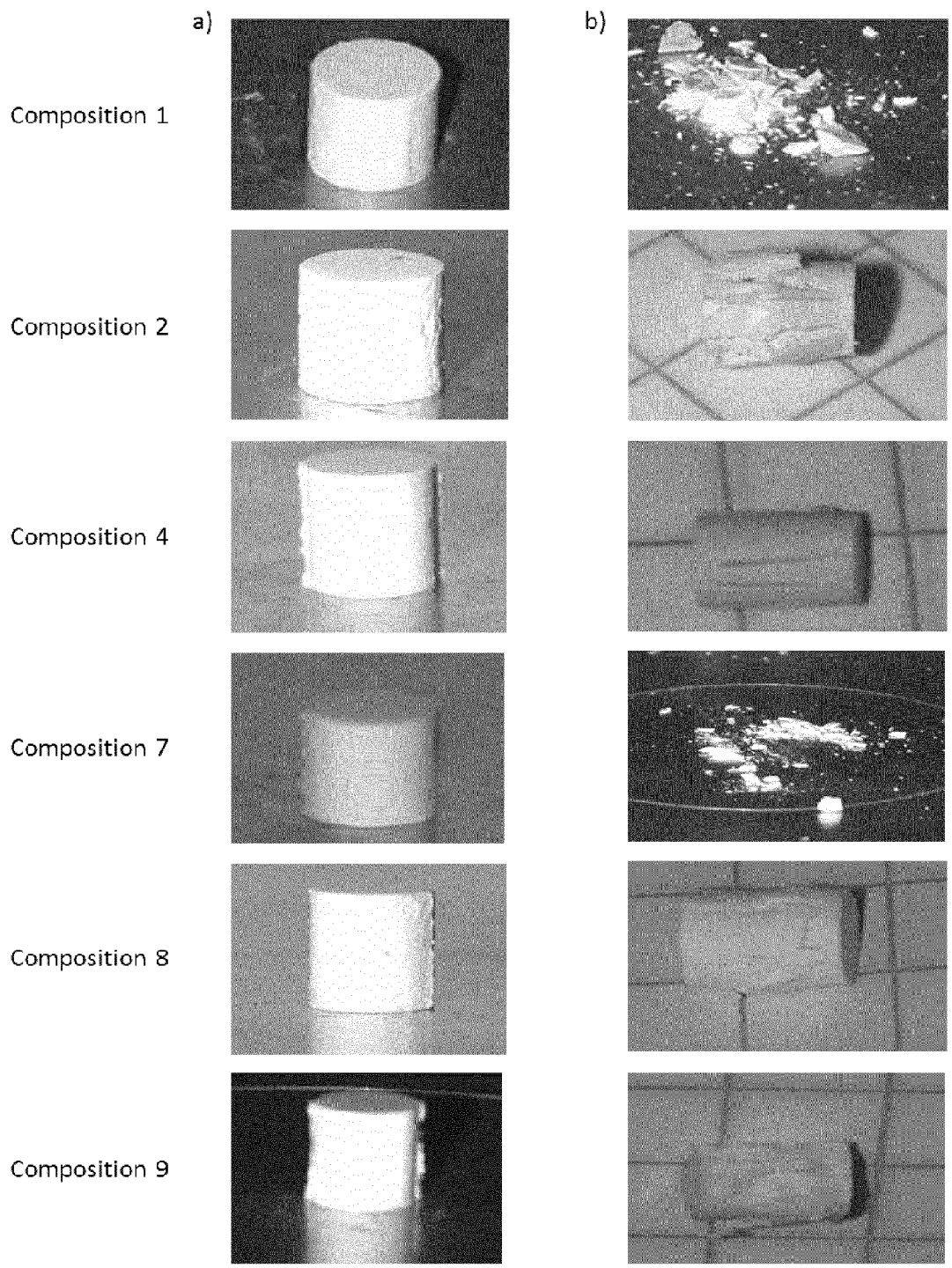

WEAR RESISTANT DENTAL COMPOSITION

CROSS-REFERENCE TO RELATED APPLICATION

This application is a national phase application under 35 U.S.C. §371 of International Application No. PCT/EP2012/068711 filed 21 Sep. 2012, which claims priority to European Patent Application No. 11182238.3 filed 21 Sep. 2011. The entire contents of each of the above-referenced disclosures is specifically incorporated herein by reference without disclaimer.

FIELD OF INVENTION

The present invention relates to a composition for use in the restoration of mineral substance, especially in the field of dentistry. More precisely, this invention relates to improved wear resistance dental compositions comprising dental cement reinforced by fibers and/or porous fillers.

BACKGROUND OF INVENTION

In the present invention, the term restoration refers to the reconstitution of decayed teeth due to a shock, a viral or bacterial infection such as decays, especially the filling of cavities.

Amalgams and resin composites are still the most widely used materials for dental crowns restoration because of their excellent mechanical properties and their easy application. Amalgams allow a period of closure on average of 14 years, which is however reduced to only about 7 years for resins composites. Even used for a long time to restore dental crowns, silver amalgams that include mercury in their formulations cause problems with patient safety in case of release in the saliva. Moreover, their metallic appearance is unsightly. Resins composites that have been proposed as an alternative to silver amalgam to solve the aesthetic problem, present a short effective setting time.

The glass ionomer cements which have also been developed, proposed a possible aesthetical solution, but have disadvantages that have generally limited their use for the filling of teeth: it is impossible to place them in direct contact with the pulp tissue and strength is limited.

Obtaining improved mechanical properties, including good mechanical resistance to compression, longer life and excellent biocompatibility, is a challenge in the field of dental compositions. In fact, the dental compositions of the prior art, using Portland cement, have good biological properties but relatively poor mechanical properties.

In patent application FR 10 52631 filed on Apr. 7, 2010, the Applicant proposed improved calcium silicate based cements for dental restoration. Compositions disclosed in this patent application comprise calcium silicate crystals and calcium carbonate crystals with a specific ratio between the d50 granulometry of calcium silicate crystals and calcium carbonate crystals. This composition show an excellent biocompatibility, a good sealing, a short setting time and good mechanical properties with a compressive strength measured at one month of 300 MPa.

Improving wear resistance of dental material is a never ending issue in the art, and there always remain a need for cement compositions having improved mechanical properties. Especially, parameters that may be improved in order to obtain more sustainable restorations are gathered under the term "wear resistance" and include abrasion resistance, flexural strength, surface hardness, crack propagation and volumetric integrity of the material during compression. It is a prerequisite that additives that may be envisaged to improve these parameters should not affect working and setting times and compressive strength of the resulting composition. Moreover the consistency of the composition during working time should be controlled for easy handling by dental practitioner.

Among possible additives to be added in the composition of dental cements, the Applicant envisaged the addition of fibers in dental cements. Even though fibers were tested by their addition in resins as disclosed in international patent application WO2008/000917 or in U.S. Pat. No. 6,334,775, there are very few examples in the prior art of fibers in dental cements.

One example of prior art disclosure is U.S. Pat. No. 2,122,011, disclosing a dental cement comprising cellulose filaments treated to render them non-swelling and non-absorptive: in this patent application, cellulose fibers was claimed for improving the strength under impact of the dental cement, however the patent application does not bring any evidence related thereto, and the skilled artisan cannot find in the specification any test supporting this claim, and no data is made available with regards to compressive or flexural strength, wear resistance or crack propagation of the resulting material.

A second example of fibers in dental cements is disclosed in patent application US2008/0206716, wherein a bioactive endodontic material for filling dental cavities is disclosed, comprising calcium silicate, calcium phosphate and calcium oxide. Among a list of diverse additives, resorbable or non-resorbable fibers may be added. However, type, geometry and proportions of these fibers are not mentioned and no effect of this addition is showed or claimed.

Patent application US2008/0299093 discloses a premixed cement paste for use in medical or dental applications. The composition comprises a calcium silicate compound and a water-free liquid carrier. The cement paste remains liquid when hermetically stocked and hardens when placed in a physiological environment. This cement may optionally comprise fibrous materials such as poly-lactic acid biopolymer or poly-lactic-co-glycolic acid, aiming at enhancing physical and mechanical properties. However, the size and proportions of these fibrous additives is not specified.

It appeared to the Applicant that the prior art was poor in showing the interest and use of fibers in dental cements, and it conducted further research in order to understand how fibers, their particular geometries and their use in selected amounts proportions could really enhance wear resistance of dental cements.

In the same time, the Applicant conducted parallel research on the addition of porous fillers in dental cements. At the date of this invention, the use of porous particles was overwhelmingly disclosed in resins.

Especially, patent application US2005/025622 discloses a dental resin in which ceramic fillers of customized shape are added to improve fracture toughness performance and resistance to abrasion. These particles may be porous hollow spheres. The improvement of the mechanical properties is supposed to be linked to the mechanical interlocking of a ceramic particle with customized shape within the resin matrix.

Also, U.S. Pat. No. 4,381,918 discloses a composite of organic resin and organic porous particles for use in a dental restoration material. In this patent, inorganic porous particles are impregnated with the hardenable resin material by applying pressure. The resin penetrates through the pores of the particles leading to the binding of the particles by the hardening of the resin. The resulting structure therefore includes a contiguous inorganic phase within a resin matrix. The resulting material is reported to have good mechanical and physical properties, especially hardness.

As a professional in dental compositions, the Applicant is fully aware that an additive of interest in resins may not be adapted for cements. Despite thorough investigations in the prior art, and despite the fact that the above disclosures are now ancient, the Applicant could not find in the prior art any data related on the effect of the addition of porous fillers in dental cements.

The only prior art found relative to the use of porous fillers in non-resins dental filling material is patent application US2003/121455. This US patent application discloses a raw compact for dental purpose comprising calcium aluminate as main binding phase and expansion-compensating additives that may be porous aggregates. In this application, the solid components are mixed, granulated and compacted to form a raw compact. A ceramic material is obtained by means of first partially hydrating the raw compact with a hydration liquid and then placing it into a cavity of a tooth that needs restoration. Due to in situ complete saturation in connection with saliva secretion, the material hardens to provide ceramic material. During hydration, the raw compact undergoes an expansion and fills the tooth cavity. However, if the expansion is too important, tooth breakage may occur. The presence of porous aggregates intends to compensate expansion and thus take up inner stresses caused by dimensional changes.

Above prior art relates to a raw compact but not to a dental cement. Therefore, the only way to have information on the effect of the addition of porous fillers in dental cements was to conduct a specific research work program on this topic, which is what the Applicant did.

Surprisingly, the Applicant found that adding fibers or porous fillers or a combination thereof in a dental cement composition could lead to improved mechanical properties. Especially the present invention proposes a dental cement composition, which is resistant to abrasion and flexion, and wherein the crack propagation is limited, the surface hardness is improved and the material maintains its integrity during compression. The present invention also relates to means for manufacturing such composition.

DETAILED DESCRIPTION

This invention relates to improved wear resistance dental compositions comprising dental cement reinforced by fibers and/or porous fillers. Preferably, this cement results from the mixing of a solid phase and a liquid aqueous phase.

In a first aspect, this invention relates to a solid phase, comprising a solid composition, comprising:
a calcium silicate powder, and
at least one ingredient selected from fibers and/or porous fillers.

The solid composition of the present invention may be used for the preparation of a dental cement for use in dentistry.

Fibers
"Fibers in General"
According to one embodiment, fibers added in cements of the present invention are natural, artificial or synthetic fibers. Natural fibers are fibers found in nature. Artificial fibers are fibers obtained by the transformation of natural resources and synthetic fibers are fibers obtained by a totally chemical process.

According to one embodiment, fibers have generally a diameter ranging from 0.5 nm to 100 µm, preferably from 5 nm to 50 µm, more preferably from 10 µm to 30 µm. According to one embodiment, fibers have generally a diameter ranging from 0.5 nm to 100 nm, preferably from 3 nm to 50 nm, more preferably from 5 nm to 30 nm.

According to one embodiment, fibers have generally a diameter ranging from 0.5 µm to 100 µm, preferably from 5 µm to 50 µm, more preferably from 10 µm to 30 µm.

According to embodiment, fibers have generally a length ranging from 0.1 µm to 5 mm, preferably from 0.1 to 3 mm, more preferably from 0.3 to 2 mm. According to one embodiment, short length fibers are preferred for aesthetical aspects. Short length fibers are those having a length ranging from 0.1 µm to 1.5 mm, preferably from 1 µm to 1.3 mm.

Advantageously, short fibers improve elasticity of the material while longer fibers ensure the suture of cracks, limiting their propagation. Without willing to be bound to a theory, it is suggested that fibers ensures a stress transfer through the discontinuity of the displacement field. It seems that before cracking, fibers have no or few influence on the mechanical behavior of the material, either on compression or traction. Once the crack is initiated, fibers seem to reduce the propagation by suturing the crack.

According to one embodiment, fibers have a Young's modulus ranging from 1 to 500 GPa, preferably from 10 to 200 GPa.

According to one embodiment, fibers have a traction resistance ranging from 200 to 10000 MPa, preferably from 500 to 7500 MPa. The Young's modulus and the traction resistance may be determined using a MTS 2/M apparatus.

According to one embodiment, the ratio of the Young's modulus of the fibers and the Young's modulus of the cement matrix is ranging from 0.4 to 13.5, preferably from 0.9 to 8.5.

According to one embodiment, fibers are present in a proportion ranging 0.1 to 5%, more preferably from 0.2 to 2.5%, in weight of the total weight of the solid composition of the present invention.

The fibers used in the composition of the present invention may be smooth, right, hooked or with a specific surface texture.

"Natural Fibers"
According to one embodiment, natural fibers are selected from the group comprising animal, vegetal or mineral fibers. Natural fibers preferably are cellulosic fibers or flax fibers.

According to one embodiment, natural fibers have generally a diameter ranging from 1 to 50 µm, preferably from 10 to 30 µm, preferably from 15.5 to 23 µm, more preferably from 18.3 to 20.5 µm.

According to embodiment, natural fibers have generally a length ranging from 0.2 to 5 mm, preferably from 0.5 to 1.5 mm, preferably from 0.6 to 1 mm, more preferably from 0.8 to 0.9 mm.

According to another embodiment, the ratio of the length to the diameter of the natural fibers is ranging from 4 to 5000, preferably from 16 to 150, preferably from 26 to 65, more preferably from 39 to 50.

According to an embodiment, the ratio of the natural fibers length to the granulometry of the calcium silicate is ranging from 26 to 666, preferably from 66 to 200, preferably from 80 to 133, more preferably from 106 to 120.

According to one embodiment, natural fibers have a Young's modulus ranging from 5 to 90 GPa, preferably from 9.5 to 85 GPa, more preferably from 18 to 40 GPa.

According to one embodiment, natural fibers have a traction resistance ranging from 220 to 4100 MPa, preferably from 500 to 1800 MPa, more preferably from 700 to 1590 MPa.

"Artificial Fibers"

According to one embodiment, artificial fibers are for example viscose, modal, lyocell, poly-lactic acid or nanocellulose. According to a preferred embodiment, fibers used in cements of the present invention are fibers of nanocellulose. Nanocellulose is a material formed of cellulose fibrils, extracted from the wood pulp.

According to one embodiment, artificial fibers are nanocellulose fibers having a diameter ranging from 1 to 35 nm, preferably from 3 to 25 nm, preferably from 4 to 22 nm, more preferably from 5 to 20 nm. In this embodiment, artificial fibers have generally a length ranging from 0.1 to 100 μm, preferably from 1 to 50 μm, more preferably from 1.5 to 20 μm. According to another embodiment, the ratio of the length to the diameter of the artificial fibers is ranging from 40 to 10000, preferably from 50 to 6250, more preferably from 75 to 4000. According to an embodiment, the ratio of the artificial fibers length to the granulometry of the calcium silicate is ranging from 0.13 to 4, preferably from 0.16 to 3.3, more preferably from 0.2 to 2.7.

According to another embodiment, artificial fibers have a diameter ranging from 0.03 to 100 μm, preferably from 1 to 50 μm, more preferably from 2 to 15 μm.

According to one embodiment, artificial fibers have generally a length ranging from 1 to 800 μm, preferably from 50 to 500 μm more preferably from 300 to 400 μm.

According to one embodiment, artificial fibers have a Young's modulus ranging from 1 to 500 GPa, preferably from 10 to 400 GPa. According to one embodiment, artificial fibers have a traction resistance ranging from 500 to 10000 MPa, preferably from 3000 to 8000 MPa. Especially, the Young's modulus of nanocellulose may range from 140 to 220 GPa. Nanocellulose may have a traction resistance ranging from 1 to 10 GPa, preferably of about 7.5 GPa.

"Synthetic Fibers"

According to one embodiment, synthetic fibers are for example polyolefines fibers such as polyethylene or polypropylene, polyvinyl fibers such as polyvinyl alcohol or polyacrylic fiber, polyester fibers such as polyethylene terephthalate, polyamide fibers, aramid (AR) fibers or polyacrylamide fibers or glass fibers or carbon fibers. According to a preferred embodiment, fibers used in cements of the present invention are para-aramid fibers, polyvinyl alcohol (PVA) fibers or polyethylene terephthalate (PET) fibers, especially high tenacity PET fibers.

According to one embodiment, synthetic fibers have generally a diameter ranging from 1 to 40 μm, preferably from 2 to 35 μm, more preferably 5 to 30 μm.

According to embodiment, synthetic fibers have generally a length ranging from 0.05 to 5 mm, preferably from 0.1 to 3.5 mm, more preferably from 0.5 to 2 mm. According to a first embodiment, short synthetics fibers are fibers having a length ranging from 0.1 to 1.5 mm, preferably from 0.7 to 1.3 mm. According to a second embodiment, long synthetics fibers are fibers having a length ranging from more than 1.5 to 5 mm, preferably from 1.5 to 2 mm.

According to another embodiment, the ratio of the length to the diameter of the synthetic fibers is ranging from 1 to 5000, preferably from 3 to 1750, more preferably from 16 to 400.

According to an embodiment, the ratio of the synthetic fibers length to the granulometry of the calcium silicate is ranging from 6 to 666, preferably from 13 to 466, more preferably from 66 to 266. According to one embodiment, synthetic fibers have a Young's modulus ranging from 1.25 to 200 GPa, preferably from 19 to 180 GPa, more preferably from 40 to 144 GPa. Especially, the Young's modulus is of about 40 GPa for PVA fibers and about 115 to 144 GPa for AR fibers.

According to one embodiment, synthetic fibers have a traction resistance ranging from 210 to 4000 MPa, preferably from 1100 to 4000 MPa, more preferably from 1830 to 4000 MPa.

Porous Fillers

Without willing to be bound to a theory, it is suggested that porous fillers ensures a better maintenance of the particles in the matrix, thus decreasing the wear of the material. In addition, porous filler may increase hardness.

According to a first embodiment, the porous fillers are mineral porous or mesoporous fillers, in solid form. According to an embodiment, all or part of the porous fillers present in the composition of the invention may or may not be silica. According to one embodiment, porous fillers may comprise a porous radio-opacifying agent. Preferred porous fillers are porous silica beads, porous ceramic beads, glass beads and/or zirconium oxide porous particles.

The beads may or may not be spherical. In a preferred embodiment, the mean diameter of the porous fillers is less than 15 μm, preferably ranging from 1 to 15 μm, more preferably from 4 to 8 μm.

In an embodiment, the porous fillers included in the solid composition of the invention have a pore size ranging from 1 to 500 nm, preferably from 5 to 250 nm; more preferably from 10 to 200 nm, more preferably from 20 to 150 nm, more preferably from 35 to 110 nm.

In another embodiment, the porous fillers included in the solid composition of the invention have a pore volume of ranging from about 10 to 10 000 mm$^3$/g, preferably from 100 to 2000 mm$^3$/g, more preferably from 500-1100 mm$^3$/g.

In a preferred embodiment, the amount of porous fillers ranges from 0.1 to 25%, preferably from 0.2 to 10%, more preferably from 0.5 to 5%, in weight to the total weight of the solid composition of the present invention.

Preferably, the d10 of the porous fillers is ranging from 0.1 to less than 5 μm, preferably less than 4 μm. Preferably, the d50 of the porous fillers is ranging from 1 to 15 μm, preferably from 2 to 10 μm, more preferably from 4 to 8 μm. Preferably, the d97 of the porous fillers is ranging from 8 to 30 μm, preferably from 9 to 25 μm, more preferably from 10 to 23 μm.

According to an embodiment, the porous fillers may have been submitted to a surface treatment prior to their introduction in the solid composition. The surface treatment may be for example silanization in order to modulate the surface properties such as hydrophilicity or adhesive interaction with medium or environment.

In an embodiment, the porous filler is adsorbed with a material capable to improve the aesthetic of the final composition, or to have a sanitizing effect such as antimicrobial agents.

Fibers and Porous Fillers

In an embodiment, the solid composition of the invention comprises both porous fillers and fibers. Without willing to be bound to a theory, it is suggested that the combination of fibers with porous fillers ensures the limitation of crack propagation, decreases the wear of the material and increases hardness.

In an embodiment, the solid composition of the invention comprises:
a calcium silicate powder,
a set accelerator in the form of a powder,
a reinforcing filler in a solid form, preferably in the form of a powder,
an radio-opacifying agent in a solid form, preferably in the form of a powder,
at least one complementary ingredient selected from solid fibers and/or solid porous fillers,
and
optionally solid pigments, preferably in the form of a powder.

In one embodiment, the calcium silicate powder is a tricalcium silicate $Ca_3SiO_5$ powder or a dicalcium silicate $Ca_2SiO_4$ powder or a mixture of tricalcium silicate and dicalcium silicate powder. Preferably, the amount of calcium silicate powder in the solid composition of the invention is ranging from 50 to 90%, preferably from 55 to 88%, more preferably from 60 to 85% by weight relative to the total weight of the solid composition. Alternatively, the amount of calcium silicate powder in the solid composition of the invention is ranging from 40 to 60%, preferably from 55 to 60% and more preferably about 58% by weight relative to the total weight of the solid composition.

In one embodiment, the composition of the invention includes a set accelerator. In one embodiment, the set accelerator is in the form of a powder. According to one embodiment, the set accelerator is a calcium oxide powder. Calcium oxide accelerates hydration of calcium silicate crystals, and thus accelerates the setting. The set accelerator may be present in an amount ranging from 0 to 3%, preferably from 0.1 to 1%, more preferably from 0.2 to 0.4% by weight relative to the total weight of the solid composition. Alternatively, the set accelerator may be present in an amount ranging from 1 to 3%, preferably from 1.5 to 2.5%, more preferably about 2%.

In one embodiment, the reinforcing filler preferably is a non-porous filler, such as for example a bioactive glass, non-porous silica, montmorillonite, a calcium salt compound, a radio-opacifying agent or a mixture thereof. In one embodiment, the calcium salt compound is calcium carbonate. Calcium carbonate may be used for accelerating the hydration of dicalcium and/or tricalcium silicate. Moreover, calcium carbonate may enhance the properties of resistance to compression of the dental composition according to the invention. According to one embodiment, the reinforcing filler is present in an amount ranging from 0.1 to 20%, preferably from 1 to 18%, more preferably from 2 to 15% by weight relative to the total weight of the solid composition of the present invention. According to one embodiment, the reinforcing filler is in the form of a powder.

In a preferred embodiment, the radio-opacifying agent is for example bismuth salts such as bismuth oxide, ytterbium salts such as ytterbium fluoride, strontium carbonate, strontium salts such as strontium phosphate, barium salts such as barium sulfate, tantalum oxide, cerium oxide, tin oxide, zirconium oxide compounds, preferably zirconium oxide in combination with yttrium and radiopaque glasses containing tantalum, barium, zirconium and strontium, and mixtures thereof, preferably, the radioopacity imparting component is bismuth derivatives, such as for example bismuth oxide or bismuth carbonates or mixtures thereof, or zirconium derivatives, especially zirconium oxide alone or in combination with yttrium; or a mixture of bismuth derivatives and zirconium derivatives. The radio-contrast media increase the radioopacity of the composition of the invention, allowing the X-ray inspection of the restoration carried out by the practitioner. Preferably, the amount of radio-opacifier agent is ranging from 2 to 40%, preferably from 4 to 38%, more preferably from 5 to 35% by weight relative to the total weight of the solid composition. Alternatively, the amount of radio-opacifier agent is preferably ranging from 30 to 40%, more preferably from 34 to 38% and even more preferably about 36% by weight relative to the total weight of the solid composition. In a preferred embodiment, the radio-opacifier, preferably zirconium oxide, has a particle size of the same order of magnitude as the reinforcing filler and calcium silicate. Preferably, the d10 of zirconium oxide is ranging from 0.1 to 0.8 µm, preferably from 0.15 to 0.5 µm, more preferably about 0.2 µm. Preferably, the d50 of zirconium oxide is ranging from 1 to 8 µm, preferably from 1.5 to 5, more preferably from 2 to 3 µm. Preferably, the d90 of zirconium oxide is ranging from 6 to 15 µm, preferably from 6.5 to 10 µm, more preferably is about 7 µm. In a preferred embodiment, the ratio of calcium silicate grain size d50 and d50 particle size of the radio-opacifier is less than 10, preferably this ratio is 0.1 to 9, most preferably 0.2 to 5, even more preferably 0.5 to 4. According to one embodiment, the radio-opacifier is in the form of a powder.

In one embodiment, solid fibers are as described above. According to one embodiment, the solid composition of the present invention comprises solid fibers. Fibers may be present in an amount ranging from 0.1 to 5%, preferably from 0.2 to 2.5% by weight relative to the total weight of the solid composition. Alternatively, the amount of fibers is preferably ranging from 2.5 to 4.5%, more preferably about 3% by weight relative to the total weight of the solid composition.

In one embodiment, solid porous fillers are as described above. According to one embodiment, the solid composition of the present invention comprises solid porous fillers. Porous fillers may be present in an amount ranging from 0.1 to 25%, preferably from 0.5 to 5% by weight relative to the total weight of the solid composition.

According to one embodiment, the solid composition of the present invention comprises solid fibers and solid porous fillers.

In one embodiment, the composition of the invention further includes pigments, preferably iron oxides. Advantageously, said iron oxides are selected from iron oxide yellow, red and brown. Preferably, the composition comprises less than 1.5%, preferably 0.02 to 1%, more preferably 0.05 to 0.5% by weight of the pigments relative to the total weight of the solid composition.

In one embodiment, the solid composition according to the invention comprises:
tricalcium silicate,
calcium oxide,
a reinforcing filler such as for example calcium carbonate,
zirconium oxide,
at least one complementary ingredient selected from solid fibers and/or solid porous fillers,
and
optionally solid pigments.

In one embodiment, the solid composition according to the invention is not a raw compact.

In one embodiment, the solid composition according to the invention does not comprise calcium aluminate.

In one embodiment, the solid composition according to the invention is not for being directly placed in a tooth cavity.

In a second aspect, the invention also relates to a kit of parts for the preparation of a composition suitable for use in dentistry of the invention, comprising a first container containing a solid phase including the above-described solid composition; and a second container containing an aqueous phase comprising water, optionally a set accelerator, preferably a calcium salt, and optionally a water-reducing agent; said first container being designed and suitable for the mixing of the solid phase with the liquid phase in a ratio solid/liquid ranging from 2 to 4.5, preferably from 3 to 4.

The invention also relates to a kit of parts for the preparation of a composition suitable for use in dentistry of the invention, comprising a container, said container comprising at least two cells, the first cell comprising a solid phase including the above-described solid composition and the second cell comprising an aqueous phase comprising water, optionally a set accelerator, preferably a calcium salt, and optionally a water-reducing agent; said container being designed and suitable for the mixing of the solid phase with the liquid phase in a ratio solid/liquid ranging from 2 to 4.5, preferably from 3 to 4.

In an embodiment, the aqueous phase comprises a water-reducing agent, such as a modified polycarboxylate copolymers solution. Advantageously, the aqueous phase of the invention comprises 0.5 to 5%, preferably 0.1 to 2.5% by weight of water-reducing agent, relative to the total weight of the aqueous phase.

In an embodiment, the water-reducing agent which may be present is a means for imparting fluidity and plasticity on the material obtained after mixture of the solid phase with the aqueous phase according to the invention, making it easier for the practitioner to mix and handle the material.

In an embodiment, the aqueous phase comprises a set accelerator, such as a calcium salt. In an embodiment, the calcium salt is calcium chloride, more preferably dehydrated calcium chloride. Advantageously, the aqueous phase of the invention comprises 5 to 32%, preferably 20 to 30%, more preferably about 29.4% by weight of set accelerator, relative to the total weight of the aqueous phase.

In an embodiment, the aqueous phase comprises fibers. In this embodiment, fibers may be in suspension in the aqueous phase.

In a preferred embodiment, the solid phase comprises solid porous fillers and the aqueous phase comprises fibers.

In a third aspect, this invention relates to a method for manufacturing a composition suitable for use in dentistry of the invention, comprising mixing a solid phase comprising the solid composition of the present invention and an aqueous phase; for example using a classic vibrating mixer with 4200 to 4500 oscillations per minute for 10 to 50 seconds, typically 30 seconds; the ratio of solid phase to liquid phase ranging from 2 to 4.5, preferably from 3 to 4.

In a fourth aspect, this invention relates to a dental cement comprising fibers or porous fillers or a mixture thereof. Preferably, this cement results from the mixing of a solid phase comprising the solid composition of the present invention and an aqueous phase, as described above.

It was observed that the overall mechanical properties of the dental cements are improved or at the least constant when fibers and/or porous or mesoporous fillers are added in the cement composition. Especially, the dental cement of the invention shows a compressive strength of at least 150 MPa, generally ranging from 180 to 250 MPa at 24 hours. According to one embodiment, the flexural strength of the dental cement of the invention is of at least 11 MPa. According to one embodiment, the microhardness after 24 hours of the dental cement of the invention ranges from 25 to 90 HV, preferably from 30 to 60 HV.

When fibers are present, the crack propagation is highly limited and the flexural strength of the composition is increased of about 25 to 30%, more preferably of about 25 to 60%. The dental cement of the invention, when it includes fibers, further shows a very good volumetric integrity. According to one embodiment, fibers are orientated in the dental cement of the invention. According to another embodiment, fibers are not orientated in the cement and are randomly dispersed within the cement.

When porous fillers are present, the microhardness of the dental cement is improved of at least 10%.

Further, the dental cement has a good dimensional stability during its placement and shows a good adhesion to the mineral substance that it is intended to restore.

The dental cement of the invention shows a most satisfactory biocompatibility.

DEFINITIONS

In the present invention, the following terms have the following meanings:

"about" refers to plus or minus ten percent of the number, parameter or characteristic so qualified.

"biocompatibility": refers to a well supported biomaterial eliciting little or no immune response in a given organism, "radio-opacifying agent" and "radio-opacifier" refers to a substance that will not allow X-rays or similar radiation to pass.

"set accelerator" refers to an agent which reduces the setting time of a material when added to said material.

"working time" refers to the period of time measured from the end of mixing during which it is possible to manipulate the composition of the invention, according to the criteria and conditions described in 7.3 of ISO 6876/2001, without any adverse effect on its properties.

"setting time" refers to the period of time measured from the end of mixing until the composition of the invention has set, according to the criteria and conditions described in 7.4 of ISO 6876/2001.

"natural fibers" refers to fibers found in nature. Animal fibers are for example hairs or animal secretions. Vegetal fibers are for example taken from seeds, stems, leaves, fruits or sap.

"artificial fibers" refers to fibers obtained by the transformation of natural resources.

"synthetic fibers" refers to fibers obtained by totally chemical processes.

a "d10" value means that 10% of the material have a value inferior to said d10 value.

a "d50" value means that 50% of the material have a value inferior to said d50 value.

a "d90" value means that 90% of the material have a value inferior to said d90 value.

a "d97" value means that 97% of the material have a value inferior to said d97 value.

BRIEF DESCRIPTION OF THE DRAWINGS

FIG. 1 is a series of photographs showing test specimens a) before and b) after compressive strength tests for different compositions.

EXAMPLES

The present invention is further illustrated by the following examples which are provided by way of illustration only and should not be considered to limit the scope of the invention.

Example 1

Compositions Comprising Fibers and/or Porous Fillers

Compositions 1 to 12 results from the mixture of 150 to 180 μL of the aqueous phase with 700 mg of solid phase 1 to 12 respectively. The mixture is achieved in a mixing device, such as Vibreur Linea Tac of Montegrosso d'Asti, at 4200 to 4500 oscillation per minute for 1 to 50 seconds, preferably 30 seconds. After mixing, compositions are immediately kneaded by the practitioner.

Aqueous Phase

The aqueous phase consists in:
29.4% of calcium chloride dehydrate,
2% of glenium commercialized by BASF
68.6% of purified water,
proportions being expressed in weight of the total weight of the aqueous phase.

Solid Phases

The composition of solid phases 1 to 21 is detailed in Table 1.

TABLE 1

| | \multicolumn{7}{c|}{Solid phases.} |
|---|---|---|---|---|---|---|---|
| | tricalcium silicate | calcium carbonate | calcium oxide | Zirconium oxide | Zirconium glass | Fibers | Porous fillers |
| 1 | 84.75% | 5% | 0.25% | 10% | \ | \ | \ |
| 2 | 82.75% | 5% | 0.25% | 10% | \ | 2% AR (1.5 mm) | \ |
| 3 | 83.75% | 5% | 0.25% | 10% | \ | 0.5% AR (0.7 mm), 0.5% AR (1.5 mm) | \ |
| 4 | 83.75% | 5% | 0.25% | 10% | \ | 0.5% AR (0.7 mm), 0.5% PVA (1.3 mm) | \ |
| 5 | 83.75% | 5% | 0.25% | 10% | \ | 0.5% AR (1.5 mm), 0.5% PVA (1.3 mm) | \ |
| 6 | 83.75% | 5% | 0.25% | 10% | \ | \ | 1% Porous glass |
| 7 | 82.75% | 5% | 0.25% | 10% | \ | \ | 2% Porous glass |
| 8 | 82.25% | 5% | 0.25% | 10% | \ | 0.5% AR (1.5 mm) | 2% Porous glass |
| 9 | 82.25% | 5% | 0.25% | 10% | \ | 0.5% PVA (1.3 mm) | 2% Porous glass |
| 10 | 82.25% | 5% | 0.25% | 10% | \ | 0.5% AR (0.7 mm) | 2% Porous glass |
| 11 | 81.75% | 5% | 0.25% | 10% | \ | 0.5% AR (0.7 mm), 0.5% PVA (1.3 mm) | 2% Porous glass |
| 12 | 81.75% | 5% | 0.25% | 10% | \ | 0.5% AR (0.7 mm), 0.5% PVA (1.3 mm) | 1% Porous glass |
| 13 | 83.75% | 5% | 0.25% | 10% | \ | 0.5% AR (0.7 mm) + 0.5% flax (0.82 mm) | \ |
| 14 | 83.75% | 5% | 0.25% | 10% | \ | 0.5% PVA (1.3 mm) + 0.5% flax (0.82 mm) | \ |
| 15 | 82.75% | 5% | 0.25% | 10% | \ | 2% flax (0.82 mm) | \ |
| 16 | 81.75% | 5% | 0.25% | 10% | \ | 0.5% PVA (1.3 mm) + 0.5% flax (0.82 mm) | 2% Porous glass |
| 17 | 81.75% | 5% | 0.25% | 10% | 2% | 0.5% PVA (1.3 mm) + 0.5% flax (0.82 mm) | \ |
| 18 | 81.75% | 5% | 0.25% | \ | 12% | 0.5% PVA (1.3 mm) + 0.5% flax (0.82 mm) | \ |

TABLE 1-continued

| | Solid phases | | | | | | |
|---|---|---|---|---|---|---|---|
| | tricalcium silicate | calcium carbonate | calcium oxide | Zirconium oxide | Zirconium glass | Fibers | Porous fillers |
| 19 | 69.75% | 5% | 0.25% | \ | 24% | 0.5% PVA (1.3 mm) + 0.5% flax (0.82 mm) | \ |
| 20 | 82.25% | 5% | 0.25% | 10% | \ | 0.5% flax (0.82 mm) | 2% Porous glass |
| 21 | 81.75% | 5% | 0.25% | 10% | \ | 1% flax (0.82 mm) | 2% Porous glass | wherein
AR: aramid (from Schwarzwälder Textil-Werke)
PVA: polyvinyl alcohol (from Schwarzwälder Textil-Werke)
flax fibers: natural fibers (from IFTH)
Porous glass (from VitraBio GmbH) has the following characteristics:
pore size: 35-50 nm,
pore volume: 600-1000 mm$^3$/g,
particle size distribution: $d_{97}$ = 10-15 μm, $d_{50}$ = 4-8 μm, $d_{10}$ = 1-4 μm
Proportions are expressed in weight of the total weight of the solid phase.
Entry 1 serves as control composition.

Example 2

Measure of Compressive Strength—Volumetric Integrity of the Dental Cement of the Invention Compressive strength is a classical mechanical evaluation of the dental biomaterials (ISO 9917:2007). The compressive strength is determined by applying a steadily increasing compressive stress to a cylindrical specimen until its fractures.

Solid and aqueous phases were mixed according to the instructions specific to the material to be tested. The mixed materials were inserted into cylindrical Teflon moulds with 6 mm high×4 mm diameter and allowed to set in a humidity chamber at 37° C. and 100% of relative humidity according to their required setting time. 6 specimens of each material were prepared. The specimens were separated from the moulds, transferred into a test tube with 0.5 mL of distilled water, stored in a beaker containing distilled water and leave in the humidity chamber at 37° C. for 24 hours or 7 days. These conditions allow the simulation of the clinical application. Then, the specimens were polished on a STRUERS LaboPol 5, with a 1200-grit SiC abrasive paper using a rotational polishing device before testing.

Compressive strength was evaluated 24 hours or 7 days after mixing of solid and liquid phases on a MTS 2/M apparatus, results are presented in table 2.

Addition of fibers and/or porous fillers does not affect significantly the compressive strength of the compositions.

The volumetric integrity of the test specimens after the compressive strength test (after 24 hours) was qualitatively evaluated (FIG. 1). Without any addition (entry 1) or with addition of porous fillers (entries 6 and 7), test specimens are totally desegregated after the compression test. On the contrary, when fibers are added (entries 2-5, 13-15 and 17-19), test specimens present only a slight, if any, deformation. The same may be observed when fibers and porous fillers are added (entries 8-12, 16, 20 and 21). The conservation of the integrity of the test specimens is representative of the limitation of crack propagation.

Example 3

Measure of Flexural Strength—Integrity of the Material

Flexural strength is one of the most classical mechanical evaluation of the dental biomaterials (ISO 4049:2009). The application of a bending force to a beam induces both compressive and tensile forces, and therefore the results should indicate a combined property.

Solid and aqueous phases were mixed according to the instructions specific to the material to be tested. The mixed materials were inserted into rectangular stainless steel moulds with a length×width=25×2 mm and a thickness of 2 mm and allowed to set in a humidity chamber at 37° C. and 100% of relative humidity for an hour. 5 samples of each material were prepared. The specimens were separated from the moulds, polished on a STRUERS LaboPol 5, with a 500-grit SiC abrasive paper, transferred into a test tube with 2 mL of distilled water, stored in a beaker containing distilled water and leave in the humidity chamber at 37° C. for 24 hours before testing. These conditions allow the simulation of the clinical application.

Flexural strength was evaluated 24 hours after mixing of solid and liquid phases on a MTS 2/M apparatus, results are presented in table 2.

Generally speaking, addition of fibers affect the flexural strength increasing it in a range from 25 to 60% and test specimens remain intact after the flexural test, not being broken.

Addition of porous fillers does not have significant effect on the flexural strength and does not affect the integrity of the material since test specimens are broken at the end of the flexural test.

Addition of fibers and porous fillers increases the flexural strength in a range from 25 to 100% and test specimens remain intact after the flexural test, not being broken.

Example 4

Measure of Microhardness

Microhardness is another classical mechanical evaluation of the dental biomaterials. Hardness is the resistance of a material to plastic deformation typically measured under an indentation load.

Solid and aqueous phases were mixed according to the instructions specific to the material to be tested. The mixed materials were inserted into moulds with 3 mm high×6 mm diameter and allowed to set according to their required setting time in a humidity chamber at 37° C. and 100% of relative humidity. 3 samples of each material were prepared. The specimens were separated from the moulds, transferred into a test tube with distilled water, stored in a beaker with distilled water and leave in the humidity chamber at 37° C. for 24 hours before testing. These conditions allow the simulation of the clinical application.

Microhardness was evaluated 24 hours after mixing with a Leco Microhardness Tester LM700AT, results are presented in table 2.

While addition of fibers does not have any effect on the microhardness of the material, addition of porous fillers increases it significantly. Addition of fibers and porous fillers also increases the microhardness of the material.

TABLE 2

Physical and mechanical properties

| Entry | compressive strength - 24 h (MPa) | compressive strength - 7 days (MPa) | integrity after compressive test 24 h | flexural strength (MPa) | integrity after flexural test | micro hardness (HV) |
|---|---|---|---|---|---|---|
| 1 | 218 | 240 | NO | 12 | NO | 35.60 |
| 2 | 195 | 238 | YES | 17.9 | YES | 38.98 |
| 3 | 203 | 215 | YES | 12 | YES | 32.62 |
| 4 | 195 | 239 | YES | 11 | YES | 36.54 |
| 5 | 240 | 270 | \ | 14.3 | YES | \ |
| 6 | 248 | 249 | NO | 11.5 | NO | \ |
| 7 | 243 | 242 | NO | 13.8 | NO | 48.58 |
| 8 | 216.5 | 239.5 | YES | 14.5 | YES | 46.33 |
| 9 | 238.5 | 282 | YES | 16 | YES | \ |
| 10 | 246 | 288 | NO | 17.6 | YES | \ |
| 11 | 252 | 273 | YES | 16 | YES | \ |
| 12 | 240 | 296 | YES | 17.5 | YES | \ |
| 13 | 182 | 237 | YES | 17 | YES | \ |
| 14 | 193 | 262 | YES | 21 | YES | \ |
| 15 | 186 | 219 | YES | 19 | YES | \ |
| 16 | 211 | 253 | YES | 19 | YES | \ |
| 17 | 213 | 248 | YES | 18 | YES | \ |
| 18 | 244 | 282 | YES | 14 | YES | \ |
| 19 | 252 | \ | YES | 17 | YES | \ |
| 20 | 245 | 274 | YES | 22 | YES | \ |
| 21 | 222 | 240 | YES | 24 | YES | \ |

The invention claimed is:

1. A solid composition comprising:
a calcium silicate powder;
a set accelerator in the form of a powder;
a reinforcing filler in a solid form;
a radio-opacifying agent in a solid form; and
at least one complementary ingredient selected from
solid fibers in an amount of 0.1% to 5% by weight of the total weight of the composition and
solid porous fillers in an amount of 0.1% to 25% by weight of the total weight of the composition.

2. The solid composition of claim 1, further comprising a solid pigment.

3. The solid composition of claim 1, comprising said solid fibers, the fibers selected from the group consisting of natural fibers, artificial fibers, and synthetic fibers.

4. The solid composition of claim 3, wherein said solid fibers are selected from the group consisting of cellulosic fibers, flax fibers, polylactic acid fibers, nanocellulose fibers, polyvinyl alcohol fibers, and aramid fibers.

5. The solid composition of claim 1, comprising said solid fibers, wherein the fibers have a length of from 0.1 μm to 5 mm.

6. The solid composition of claim 1, comprising said solid fibers, wherein the fibers have a diameter of from 0.5 nm to 100 μm.

7. The solid composition of claim 1, comprising said porous fillers, the fillers selected from the group consisting of mineral porous fillers, and mesoporous fillers.

8. The solid composition of claim 7, wherein said porous fillers are selected from the group consisting of porous silica beads, porous ceramic beads, glass beads, and zirconium oxide porous particles.

9. The solid composition of claim 1, comprising said porous fillers, the fillers having a pore size of from 1 to 500 nm.

10. The solid composition of claim 1, comprising said porous fillers, the fillers having a pore volume of about 10 to 10,000 mm$^3$/g.

11. The solid composition of claim 1, comprising said porous fillers and said fibers.

12. The solid composition of claim 1, comprising:
a calcium silicate powder comprising tricalcium silicate, dicalcium silicate, or a mixture thereof;
a set accelerator comprising calcium oxide;
a reinforcing filler comprising calcium carbonate;
a radio-opacifying agent; and
at least one complementary ingredient selected from said solid fibers and/or said solid porous fillers.

13. The solid composition of claim 12, wherein the radio-opacifying agent is selected from the group consisting of zirconium oxide, ytterbium salts, bismuth salts, barium salts, and strontium salts.

14. A kit for the preparation of a dental cement, comprising:
a first container containing the solid composition of claim 1; and
a second container containing a liquid aqueous phase;
the first container being configured for mixing of the solid phase with the liquid aqueous phase in a solid/liquid ratio ranging from 2 to 4.5.

15. A method for preparing a dental cement, comprising mixing the solid composition of claim 1 with a liquid aqueous phase.

16. The method of claim 15, wherein the liquid aqueous phase comprises a water-reducing agent.

17. The method of claim 16, wherein the water reducing agent is a modified polycarboxylate copolymer.

18. A dental cement manufactured according to the method of claim 15.

* * * * *